United States Patent [19]

Kitayama

[11] Patent Number: 5,673,432
[45] Date of Patent: Oct. 7, 1997

[54] EYE MASK HAVING A STOPPER AND CYLINDER MOUNTED ON EACH SUPPORT MEMBER THEREOF

[76] Inventor: Hidehiro Kitayama, 2-14-4 Yanagibashi Taito-ku, Tokyo, Japan

[21] Appl. No.: 719,180

[22] Filed: Sep. 24, 1996

[30] Foreign Application Priority Data

Oct. 18, 1995 [JP] Japan ............... 7-303258

[51] Int. Cl.[6] ............................. A61F 9/04
[52] U.S. Cl. ............ 2/15; 2/449; 2/450; 351/123
[58] Field of Search ............... 2/15, 448, 449, 2/450, 451, 452, 431; 351/123, 156

[56] References Cited

U.S. PATENT DOCUMENTS

| | | | |
|---|---|---|---|
| 2,243,982 | 6/1941 | Seeley | 351/123 X |
| 2,305,080 | 12/1942 | Hemphill et al. | 2/15 |
| 2,527,027 | 10/1950 | Mull | 2/450 |
| 4,682,374 | 7/1987 | Geiser | 2/449 X |
| 4,872,217 | 10/1989 | Kitayama | 2/15 |
| 5,162,823 | 11/1992 | Goldstein | 351/123 |
| 5,435,006 | 7/1995 | Kitayama | 2/15 |

FOREIGN PATENT DOCUMENTS 3400714   7/1985   Germany ............... 351/123

*Primary Examiner*—Peter Nerbun
*Attorney, Agent, or Firm*—Cislo & Thomas LLP

[57] ABSTRACT

In an eye mask according to the present invention, a pair of support members are connected with a main body by a plurality of convex portions and receiving holes. A stopper is movably mounted to a rear portion of each said support member, whereby the eye mask is definitely and preferably fitted to a wearer's face.

1 Claim, 3 Drawing Sheets

FIG. 7
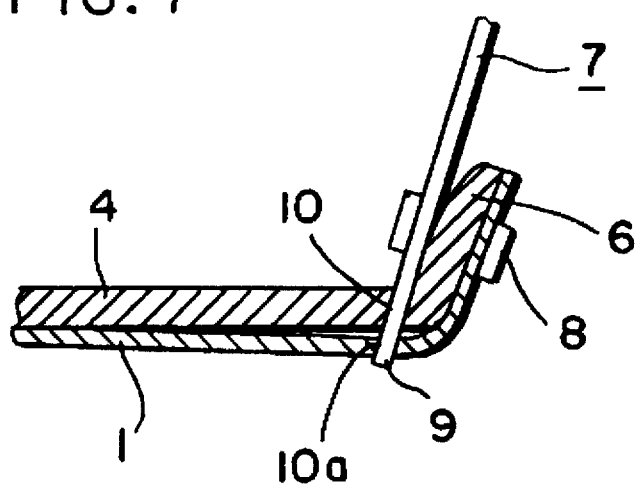
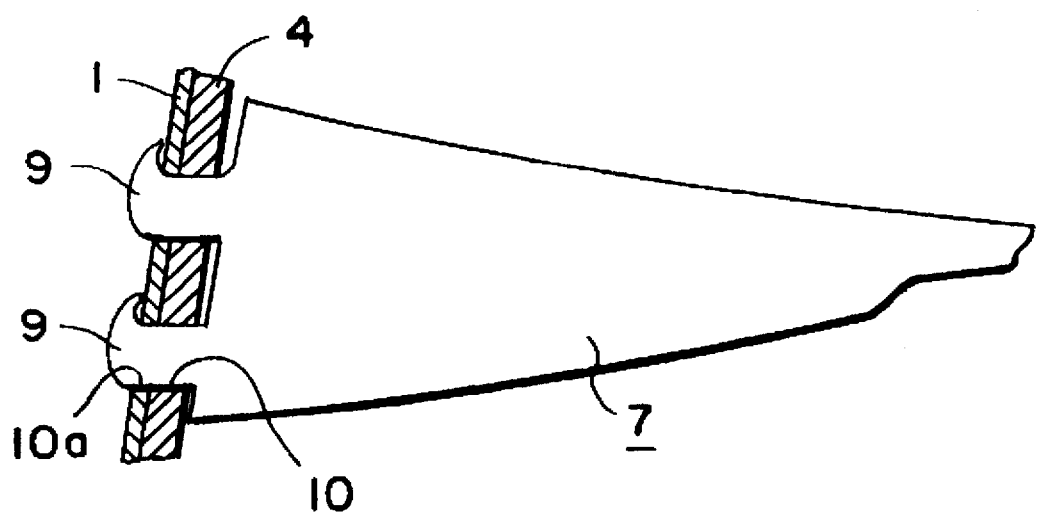
FIG. 8

EYE MASK HAVING A STOPPER AND CYLINDER MOUNTED ON EACH SUPPORT MEMBER THEREOF

BACKGROUND OF THE INVENTION

Field of the Invention

The present invention relates to an eye mask and to a novel improvement to connect the support members with a main body at right angles thereto and to definitely connect a support member with an ear by mounting a stopper with said support member.

In a conventional eye mask, an end portion of a support member is connected with a main body as one body. Alternately, said support member may be constructed by a ring-shaped cord.

Since a conventional eye mask is arranged as described above, the following problem is posed. That is, since said support members are only connected with said main body as one body, when the eye mask is removed and placed on the table, said support members are biased toward each other, and it is impossible to keep a U-shape of the eye mask.

Further, said support members are not always sufficiently fitted to an ear, and, thus, said support members may become detached from said ear.

SUMMARY OF THE INVENTION

The present invention has been made to solve the above problem, and has as its object to provide an eye mask which is designed in such a manner that the support members are connected with a main body at right angles thereto, and are definitely connected to an ear by mounting a stopper with each of said support members.

According to the present invention, there is provided an eye mask having a flexible main body which is composed of a sheet member, a plurality of small holes which are shaped to an eye portion of said main body, a pad member of ring or C-shape and having a certain thickness which is attached to a rear surface of said main body, a pair of support members which are connected to each of the side ends of said main body, and a stopper which is mounted to a rear portion of each of said support members.

According to the present invention, said stopper is movably mounted to each of said support members.

According to the present invention, said stopper is composed of a flexible O-ring and a flexible cylinder which is connected in encompassing fashion thereto.

According to the present invention, an eye mask has a pair of ear portions which are attached to opposed end portions of the main body of the eye mask and a pair of supplemental ear portions are attached thereto to provide better attachment to the wearer of the eye mask.

BRIEF DESCRIPTION OF THE DRAWINGS

FIG. 7 shows another embodiment of the invention shown in FIG. 3.

FIG. 8 shows another embodiment of the invention shown in FIG. 4.

DESCRIPTION OF THE PREFERRED EMBODIMENT

A preferred embodiment of an eye mask according to the present invention will be described below with reference to the accompanying drawings.

Figure 1:
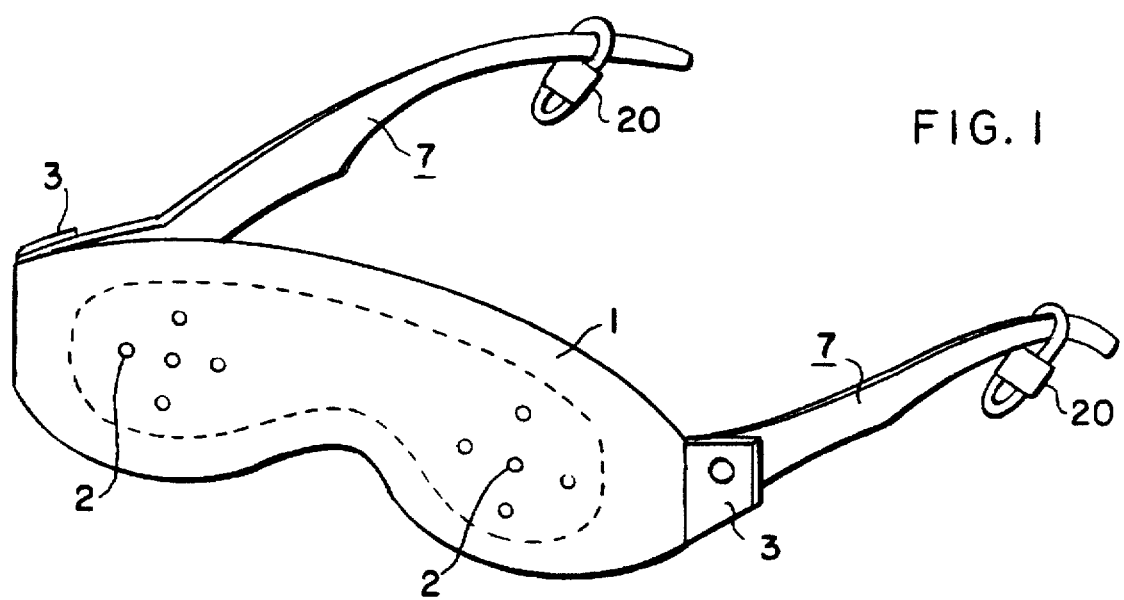
FIG. 1 shows a perspective view of the eye mask of the present invention.
Figure 2:
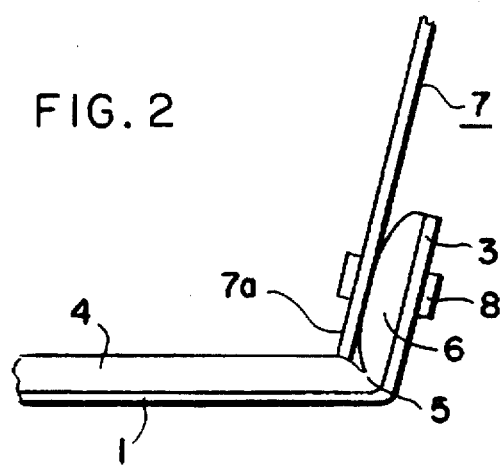
FIG. 2 shows a flat a view of a part of FIG. 1.

Reference numeral 1 in FIG. 1, denotes a main body which is composed of a flexible material, such as a sheet of synthetic resin, a plurality of small holes 2 are formed at both eye positions of said main body.

A pair of conformable ear portions 3 are formed at both end portions of said main body 1. A pad member 4 having a ring shape is attached to a rear surface of said main body 1, said pad member 4 is composed of a soft material and has.

A cutout of said pad member 4 is, as shown in dotted lines of FIG. 1 and is configured to not overlie said eye positions, and has a pair of supplemental ear portions 6 which are flexibly secured to both end portions of said pad member 4 via a conformable portion 5.

Figure 4:
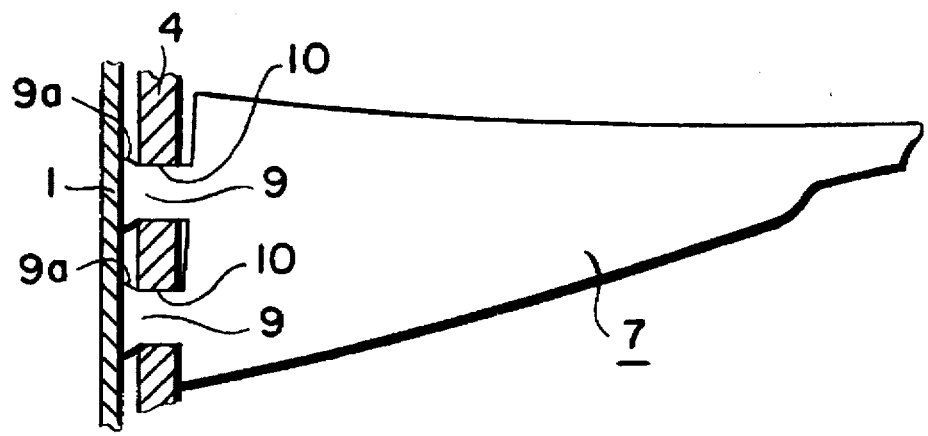
FIG. 4 shows an enlarged cross sectional view of a part of FIG. 3.
Figure 5:
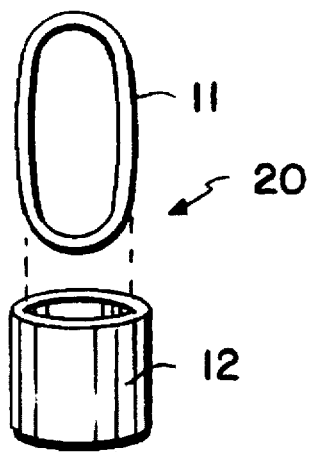
FIG. 5 shows a detailed view of the stopper of FIG. 1.
Figure 6:
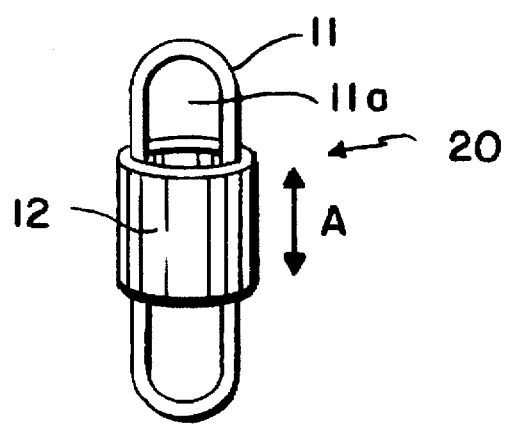
FIG. 6 shows a perspective view of FIG. 1.

A pair of support members 7 are composed of a plate member, each of which is connected to each of said ear portions 3 and supplemental ear portion 6 by a pin 8. A pair of inwardly spaced portions 9 of each ear are provided to each end portion 7a of said support member 7 and are connected to holes 10 which are provided to the inside of said supplemental ear portion 6 of said pad member 4. Enlarged portions 9a of said end portions 9 protrude towards the outside of said holes 10 whereby a connection between said end portion 9 and hole 10 is attained, as shown in FIG. 4.

Figure 3:
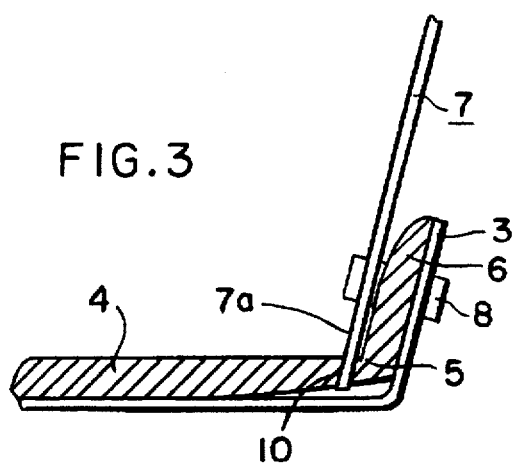
FIG. 3 shows a cross sectional view of FIG. 2.

Further said enlarged portion 9a of said end portion 9 is covered by said main body 1 and does not extend or protrude outwardly of the surface thereof as shown in FIG. 3.

Thus, end portion 7a of said support member 7 is connected with the inside of said conformable portion 5 of said pad member 4, and is thus able to maintain said ear portions 3, 6 almost at right angles against said main body 1. Specifically, they are able to keep said support member 7, which are almost at right angles against a longitudinal direction of said main body 1 and pad member 4, as configured and as shown in FIG. 1.

A stopper 20 is movably mounted to a rear portion of said support member 7, said stopper 20 is composed of an O-ring 11 such as synthetic flexible material and a cylinder 12 such as synthetic flexible material. The O-ring is inserted into said cylinder 12, said rear portion of said support portion 7 inserts into a hole portion 11a of said O-ring 11.

Further, a clamping condition of said hole portion 11a against said support member 7 is obtained to adjust a location of said stopper 20 along said support member 7.

Therefore, it is possible to definitely determine a position of said stopper 20 and to determine a position against an ear of the wearer of the eye mask.

FIG. 7 shows another embodiment of FIG. 3, wherein portion 9 protrudes through the hole 10 and another hole 10a of said main body 1, wherein holes 10a are formed at both ends of main body 1, said portions 9 are positioned on a surface of said main body 1 as shown in FIGS. 7 and 8.

Since the eye mask according to the present invention is arranged as described above, the following effect can be obtained.

More specifically, the position of the support members are determined at right angles to said main body, a stopper is mounted to each said support member whereby conformity against the wearer's ear and face is attained.

What is claimed is:

1. An eye mask comprising a flexible main body which is composed of a sheet member, a plurality of small holes which are formed on an eye portion of said main body, a pad member having a ring shape and being attached to a rear surface of said main body, a pair of support members connected to either side of said main body, each of said support members having mounted on a rear portion thereof a stopper, said stopper being composed of a flexible O-ring having disposed thereon a flexible cylinder.

* * * * *